United States Patent
Hagedorn et al.

(10) Patent No.: US 6,596,854 B2
(45) Date of Patent: Jul. 22, 2003

(54) ISOLATED NUCLEIC ACID MOLECULE ENCODING A VARIANT HUMAN EUKARYOTIC INTIATION FACTOR 4E PROTEIN

(75) Inventors: Curt H. Hagedorn, Atlanta, GA (US); Taly Spivak-Kroizman, Baytown, TX (US); Yiping Xie, Dunwoody, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/855,747

(22) Filed: Apr. 14, 2001

(65) Prior Publication Data

US 2002/0048804 A1 Apr. 25, 2002

(Under 37 CFR 1.47)

Related U.S. Application Data

(62) Division of application No. 09/465,615, filed on Dec. 17, 1999, now Pat. No. 6,232,442, which is a continuation of application No. 08/995,060, filed on Dec. 19, 1997, now abandoned.
(60) Provisional application No. 60/033,533, filed on Dec. 20, 1996.

(51) Int. Cl.$^7$ ............................................. C12N 15/12
(52) U.S. Cl. ...................................................... 536/23.5
(58) Field of Search .......................................... 536/23.5

(56) References Cited

PUBLICATIONS

Altman, M. et al., "Site–directed Mutagenesis of the Tryptophan Residues in yeast Eukaryotic Initiation Factor 4E"; (1988) *J. Biol. Chem.* 263(3):17229–17232.

Edery, I. et al., "High–level synthesis in *Escherichia coli* of functional cap–binding eukaryotic iniation factor eIF–4E and affinity purification using a simplified cap–analog resin"; (1988) *Gene* 75:517–525.

Edery, I. et al., "An Efficient Strategy to Isolate Full–length cDNAs Based on an mRNA Cap Retention Procedure (CAPture)"; (1995) *Mol. Cell Biol.* 15(16):3363–3371.

Garrity, R.R. et al., "Genetic Vaccination with Naked HIV–1 mRNA Results in Low Titered Anti–gp120 Response"; (1996) Meeting on Molecular Approaches to the Control of Infectious Diseases, Cold Spring Harbor Laboratory, Cold Spring Harbor, NY, Sep. 9–13, 1996.

Haas, D.W. and Hagedorn, C. H., "Casein Kinase I Phosphorylates the 25–kDa mRNA cap–binding Protein"; (1991) *Arch. Biochem. Biophys.* 284(1):84–89.

Hagedorn, C.H. et al., "Expression of Functional eIF–4E$_{human}$ Purification, Detailed Characterization, and its use in Isolating eIF–4E Binding Proteins"; (1997) *Protein Expression and Purification* 9(1):53–60.

Joshi–Barve, S. et al., "Alteration of the Major Phosphorylation Site of Eukaryotic Protein Synthesis Initiation Factor 4E Prevents Its Association with the 48S Initiation Complex"; (1990) *J. Biol. Chem.* 265(5):2979–2983.

Marcotrigiano J., et al., "Cocrystal structure of the Messenger RNA 5' Cap–Binding Protein (eIF4E) Bound to 7–methyl–GDP"; (1997) *Cell* 89:951–961.

Matsuo, H. et al., "Structure of translation factor eIF4E bound to m$^7$GDP and interaction with 4E–binding protein"; (1997) *Nature Struct. Biol.* 4(9):717–724.

Morino, S., et al., "Soluble Expression of a Synthetic Gene for Human Translation Initiation Factor 4E in *Escherichia coli*"; (1995) *Biol. Pharm. Bull.* 18(2):372–376.

Morino, S., et al., "Analysis of the mRNA cap–binding ability of human eukaryotic initiation factor–4E by use of recombinant wild–type and mutant forms"; (1996) *Eur. J. Biochem.*, 239(3):597–601.

Morino, S. et al., "Gene Expression of Human Eukaryotic Initiation Factor–4E for Protein Synthesis and Study of Its Recognition Mechanism of mRNA Cap Structure"; (1995) *J. of Pharm. Soc. Japan* 115(6):401–419.

Rychlik, W. et al., "Amino acid sequence of the mRNA cap–binding protein from human tissues"; (1987) *Proc. Natl. Acad. Sci. USA* 84:945–949.

Teraoka, Y. et al., "Mutation of the Cysteine Residues in Human Initiation Factor 4E: Effect on mRNA Cap Binding Ability"; *Biochem. Biophys. Res. Comm.* 228(3):704–708.

*Primary Examiner*—Terry McKelvey
(74) *Attorney, Agent, or Firm*—Greenlee, Winner and Sullivan, P.C.

(57) ABSTRACT

The invention provides a method of purifying human eIF-4E protein and amino acid sequence variants thereof having altered binding affinity for capped RNA. Using the described purification, amino acid sequence variants can readily be expressed, purified and tested. Both lowered and enhanced binding affinity variants are useful for modifying protein expression levels in vivo and in vitro.

5 Claims, 6 Drawing Sheets

ISOLATED NUCLEIC ACID MOLECULE ENCODING A VARIANT HUMAN EUKARYOTIC INTIATION FACTOR 4E PROTEIN

CROSS-REFERENCE TO RELATED APPLICATIONS

This application is a divisional of U.S. application Ser. No. 09/465,615 filed Dec. 17, 1999, now U.S. Pat. No. 6,232,442, issued May 15, 2001, which is a continuation of U.S. application Ser. No. 08/995,060 filed Dec. 19, 1997, now abandoned, which in turn claims priority from U.S. Provisional Application No. 60/033,533 filed Dec. 20, 1996.

ACKNOWLEDGEMENT OF GOVERNMENT FUNDING

Support for research leading to the invention was provided in part by the National Institutes of Health, Grants GM40219 and CA63640-02. The United States Government has certain rights in the invention.

BACKGROUND OF THE INVENTION AND PRIOR ART

In eukaryotes, protein synthesis (translation) occurs in a complex process in which messenger RNA (mRNA) carrying amino acid sequence information encoded in its nucleotide sequence interacts with ribosomes and a variety of cofactors and enzymes. Among the critical interactions are those which occur in the initial steps of mRNA recognition during initiation of translation Synthesis of mRNA occurs in the nucleus of the eukaryotic cell. Translation occurs in the cytoplasm. RNA sythesized in the nucleus is subject to modifications, generally termed processing reactions. These include capping, intron splicing and polyadenylation. Of importance herein is the processing step known as capping. Capping is the addition, at the 5' end of mRNA, of 7-methyl guanine, ($m^7G$) joined by an unusual 5'—5' diphosphate bridge to the 5' terminal ribonucleotide of mRNA. The capping reaction occurs naturally in the cell nucleus during mRNA synthesis. Capping can also be carried out in vitro in an enzyme-catalyzed reaction. Commercially available kits can be obtained, for example, from Life Technologies, Inc., Gaithersburg, Md.

The initiation of translation in the cytoplasm requires specific binding of proteins termed initiation factors. An important initiation factor in mammalian cells is the eukaryotic Initiation Factor—4E (eIF-4E) which binds to capped RNA ($m^7G$-RNA). Translation is regulated in vivo by factors and conditions which affect the binding of eIF-4E to $m^7G$-RNA, including proteins that bind to eIF-4E (4E binding proteins). For example, at least one 4E binding protein designated 4E-BP-1 acts to prevent the binding of eIF-4E to $m^7G$-RNA. 4E-BP-1, also known as PHAS-1, can undergo phosphorylation which is induced by insulin or other growth factors. The insulin-induced phosphorylation of 4E-BP-1 releases the bound eIF-4E which is now available to bind $m^7G$-RNA. This process may account for the rapid stimulation of protein synthesis in muscle tissue induced by insulin. Another eIF-4E binding protein is p220, also known as eIF-4F, a protein that binds with eIF-4E as part of a functional complex which interacts with mRNA to positively regulate translation.

The sequence of DNA encoding human eIF-4E has been determined [Reychlik, W. et al. (1987) Proc. Natl. Acad. USA 84:945–949]. Yeast eIF-4E and a fusion protein of mouse eIF-4E have been expressed in E. coli [Edery, I., et al. (1988) Gene 74:517–525; Edery, I., et al. (1995) Mol. Cell. Biol. 15:3363–3371]. Haas, D. W. et al. (1991) Arch. Biochem. Biophys. 284:84–89 reported purification of native eIF-4E from erythrocytes. Stern, B. D. et al. (1993) reported isolation of recombinant eIF-4E using denaturing concentrations of urea. However, expression and purification of recombinant human eIF from the soluble fraction without a denaturation step was not described before.

Transfection using RNA has not been widely reported. The primary difficulty is the susceptibility of RNA to RNAses and the lack of RNA restriction enzymes and ligases that has prevented in vitro recombination of RNA segments. Nevertheless, transfection with RNA has several advantages over transfection with DNA. Transfection by RNA does not normally lead to genetic alteration of host cells. Instead, a transient expression of the protein encoded by the transfecting RNA is observed. There are circumstances where such transient expression is preferable. For example, RNA transfected cells can transiently express an antigen in an individual to be immunized. Garrity, R. R., et al. (1996) (Abstr. 1996 Meeting on Molecular Approaches to the Control of Infectious Diseases, Cold Spring Harbor Laboratory, Cold Spring Harbor, N.Y., Sep. 9–13, 1996) reported that antibodies to gp 120 and gp 160 of HIV-1 were detectable in guinea pigs that had been injected intramuscularly with naked $m^7G$-RNA encoding the respective antigens. Titres were low and the antibodies did not neutralize homologous virus. Since DNA transfection leads to chromosomal integration of extraneous DNA and long-lived expression of its encoded protein, unpredictable and deleterious effects may occur in the host. Transient expression resulting from RNA transfection can avoid these concerns. The problems to be overcome with RNA transfections include extremely low transfection efficiency and short intracellular lifetime of transfected RNA.

eIF-4E has recently been shown to play a direct role in maintaining the phenotype of breast cancer cells. The levels of eIF-4E in biopsies of breast cancer and breast cancer cell lines are increased (3–30 fold; mean of 10.5±0.9) as compared to benign fibroadenomas of breast tissue and control cells [Kerekatte, V. et al. (1995) Int J Cancer 64(1):27–31; Anthony, B. et al. (1996) Int J Cancer 65:858–863]. Immunohistochemical studies showed that the cells expressing high levels of eIF-4E are indeed cancer cells and not stromal cells. In addition, evidence indicates that high levels of expression of eIF-4E correlate with a poor clinical outcome in breast cancer [Li, B. D. L. et al. (1997) Cancer 79(12):2385–2390]. A direct role for eIF-4E in breast cancer is evidenced by studies demonstrating that mammary carcinoma cells (MDA-435) exhibiting a 50% decrease in eIF-4E expression, due to stable transformation with an antisense construct, have a markedly reduced ability to produce tumors in nude mice. In addition, the down-regulation of eIF-4E expression in these cells results in relatively avascular tumors compared to control cells [Nathan, et al. 1997].

The cocrystal structure of mouse eIF-4E bound to $m^7GDP$ [Marcotrigiano J. et al. (1997) Cell 89:951–961] and the solution structure of yeast eIF-4E bound to $m^7GDP$ as determined by NMR spectroscopy [Matsuo H. et al. (1997) Nature Struct Biol.4:717–724] have been described. Both studies describe a cap-binding slot for eIF-4E in which the $m^7G$ moiety is sandwiched between the side chains of two tryptophans, Trp-56/Trp-102 in mouse and Trp-58/Trp-104 in yeast eIF-4E. A third tryptophan, Trp-166 (both mouse and yeast), as well as Glu-103 in mouse and Glu-105 in yeast, form hydrogen bonds with $m^7G$. The cocrystal structure demonstrated additional interactions involving residues Arg-157, Arg-112, and Lys-162 which make direct or water-mediated contacts with the phosphate groups of $m^7$GDP. The NMR solution structure of yeast eIF-4E showed that Arg-157, Lys-158 and Glu-159 are close to the phosphate tails of $m^7$GDP and $M^7$GTP.

SUMMARY OF THE INVENTION

The invention provides purified recombinant human eIF-4E, as well as a method of purification from transgenic cells expressing eIF-4E. Purified wild-type human eIF-4E binds in vitro to $m^7$G-RNA with a binding constant of $10.1 \pm 0.3 \times 10^5 M^{-1}$. Binding is 1:1 on a molar basis, forming a binary complex designated eIF-4E-$m^7$G-RNA. A sequence of amino acids involved in binding human eIF-4E to $m^7$G-RNA has been identified. Amino acid substitutions within the eIF-4E amino acid sequence have been made, some of which can result in 1–2 orders of magnitude tighter binding, others of which result in reduced binding. The invention therefore also provides modified human eIF-4E. The term "variant human eIF-4E" as used herein embraces amino acid substitutions, deletions and insertions and combinations thereof affecting the binding affinity of the variant eIF-4E to $m^7$G-RNA without destroying the protein's capacity to function as an initiation factor.

The wild-type and variant human eIF-4E bound to $m^7$G-RNA improves stability of $m^7$G-RNA, which enhances the transformation efficiency. Furthermore the presence of bound eIF-4E ensures immediate and efficient translation in the transfected host cell, which can be observed as enhanced expression of the protein encoded by the transfecting RNA.

The invention therefore provides a method for making eIF-4E-$m^7$G-RNA and a method for transfecting eukaryotic cells by contacting the cells with eIF-4E-$m^7$G-RNA. The method can be used with variant human eIF-4E or wild-type human eIF-4E. RNA transfected cells transiently express the protein encoded by the RNA sequence.

The invention further provides a method for isolating 4E binding proteins (4E-BP). Immobilized eIF-4E acts as an affinity ligand for the various proteins that bind to it and regulate translation. The 4E-BP proteins can thereby be isolated and characterized, in order to better understand their role in controlling translation.

The invention further provides amino acid sequence variants of human eIF-4E having either reduced or enhanced binding affinity for capped mRNA ($m^7$G-RNA). Variants having reduced binding affinity are useful in treatment of breast cancer. For example, DNA encoding a reduced-binding variant, introduced into breast cancer cells by a gene-therapy technique can act as a dominant negative mutant, counteracting the overexpression of eIF-4E required to maintain the tumor phenotype of such cells. Variants having enhanced binding affinity have increased stability in vitro and in vivo, for improved transient expression of a selected gene in RNA transfection. Similar uses of natural or varied sequence eIF-4E for temporally-limited gene regulation can be recognized by those skilled in the art, including, for example, to control the differentiation of stem cells. As a further utility, the ability of host cells to express large proteins transgenically can be enhanced by transfection using natural or variant eIF-4E.

BRIEF DESCRIPTION OF THE FIGURES

FIG. 4A shows equilibrium binding constant for recombinant eIF-4E and $m^7$GTP. The fluorescence intensity of recombinant human eIF-4E binding to $m^7$GTP as a function of $m^7$GTP concentration was measured. All solutions were prepared in buffer A at pH 7.6, 25° C. and the concentration of eIF-4E was 1 μM. An excitation wave length of 280 nm was used to monitor the fluorescence intensity at 330 nm.

FIG. 4B shows Eadie-Hofstee plot of the fluorescence changes (ΔF), used to calculate the equilibrium binding constant for the eIF-4E/$m^7$GTP complex formation.

DETAILED DESCRIPTION OF THE INVENTION

Figure 1:
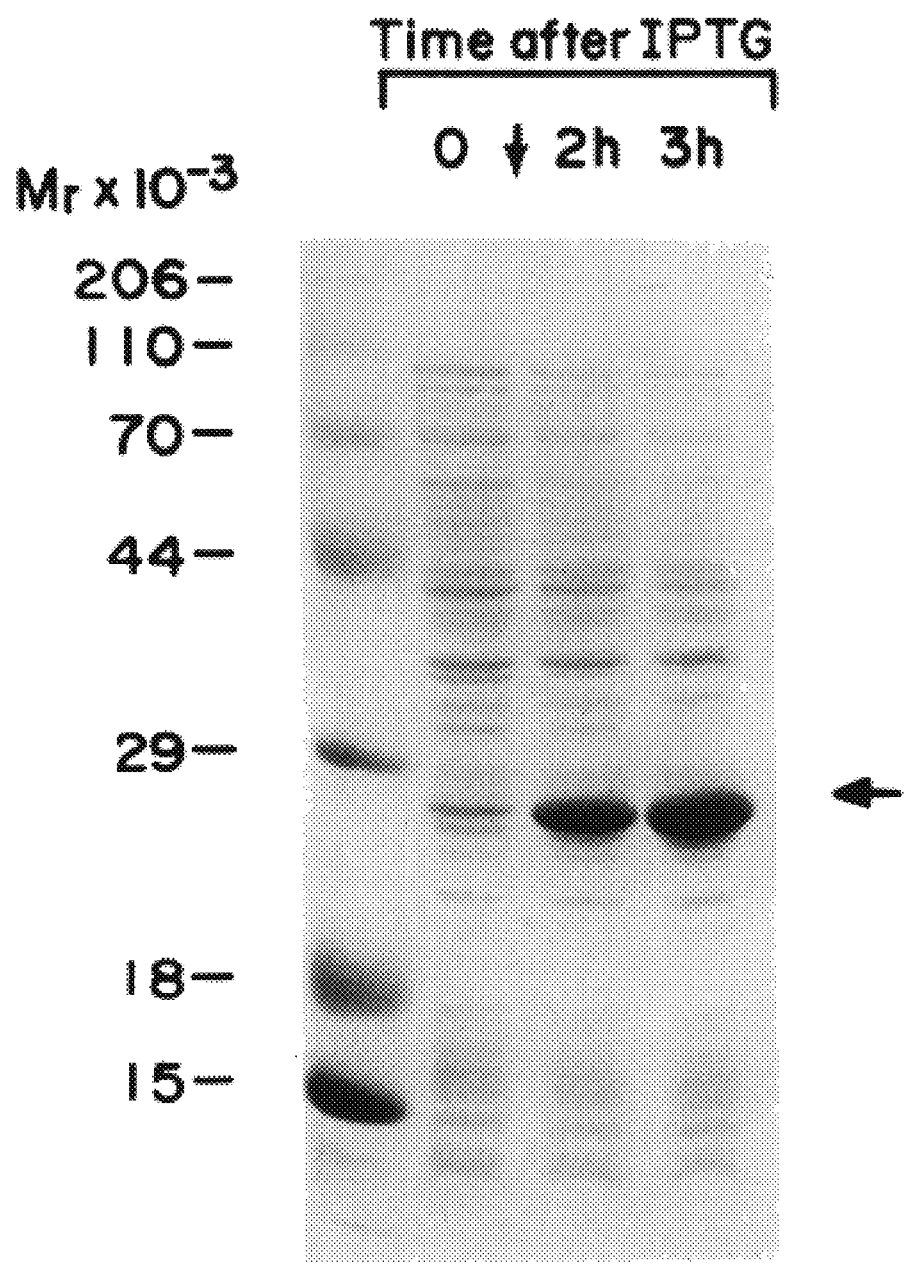
FIG. 1 shows expression of eIF-4E in *E. coli*. A photograph is shown of a Coomassie Blue stained 10% polyacrylamide gel of whole cell lysates of *E. coli* present in 0.5 ml samples of a culture immediately before, 2 h and 3 h after the addition of IPTG. The location of recombinant eIF-4E is designated by an arrow. The size of molecular mass markers present in the first lane is indicated to their left.

Little is known about the molecular details of eIF-4E interactions with $m^7$G-RNA or with regulatory proteins such as the 4E-BP proteins or with proteins of the eIF-4F complex. In order to characterize these interactions, the components thereof and their functions, sufficient quantities of purified eIF-4E must be available to the art. The present invention employs a transgenic expression system to synthesize human eIF-4E and further provides a method for purification that now provides sufficient quantities of human eIF-4E, to conduct physical and chemical studies. It now becomes possible to exploit the binding affinity of eIF-4E for capped RNA to devise a novel RNA transfection vehicle.

RNA transfection has been limited heretofore by the extreme lability of naked RNA, by the lack of practical techniques for making in vitro recombinant RNA constructs, and by a lack of transfection vectors. Nevertheless, RNA transfection has unique advantages for bio-medical applications. Whenever the goal is simply to express a gene product for a limited time, i.e., transiently, RNA transfection would be preferred. One such use, for example, is for the in vivo generation of antigens which, eliciting an immune response, serves as a means of generating immunity. The feasibility of such an approach has been demonstrated (Garrity, R. R., et al., supra). The present invention employs capped RNA bound to eIF-4E (eIF-4E-m$^7$G-RNA) as a transfection vector. Use of eIF-4E-m$^7$G-RNA, improves RNA transfection efficiency and yield in two ways; by stabilizing the transfecting RNA and by assuring expression of the RNA once it has entered the host cell. Improved stability is obtained by the protective effect of eIF-4E. Once the eIF-4E-m$^7$G-RNA has entered a host cell it can be translated immediately, without having to compete with endogenous mRNA for endogenous initiation factor. Although RNA transfection in animals has been demonstrated to occur simply by injection of "naked" capped RNA, other carriers or complexing agents are useful in nucleic acid transfections generally, as is well known in the art. Some examples include cationic lipid compounds, such as Lipofectamine™ (Life Technologies, Gaithersburg, Md.) and polycationic dendrimers, such as Starburst™ Dendrimers (Life Technologies, Gaithersburg, Md.).

Isolation of the 4E-binding proteins has been achieved using an affinity column of eIF-4E bound to a chromatographic medium. Among the proteins identified as binding to such a column were p220 and eIF-4A, 220 kDa and 48 kDa respectively [Sorenberg, N. et al. (1978) *Proc. Natl. Acad. Sci. USA* 75:4843–4847; Takara, S. M., et al. (1981) *J. Biol. Chem.* 256:7691–7694). The use of eIF-4E affinity can isolate other 4E-binding proteins as well. Other affinity strategies, for example, the use of eIF-4E-m$^7$G-RNA as an affinity capture ligand, can yield additional proteins that function in translation.

The invention includes the demonstration that human eIF-4E cDNA can be expressed in a prokaryotic host and purified as a soluble, active protein (termed recombinant human eIF-4E herein) from a lysate of a host cell culture. As expressed in *E. coli*, eIF-4E is not phosphorylated. The non-phosphorylated protein is active and has biological and physical characteristics that are similar or identical to native eIF-4E. In vitro phosphorylation of eIF-4E has a modest effect on its interaction with capped mRNA. However, phosphorylation of eIF-4E appears to affect regulation of its interaction with regulatory proteins, for example, the p220 subunit of the eIF-4F complex.

The eIF-4E protein can be purified from host cells transfected to express the protein, as one aspect of the invention. The host cells can be prokaryotic or eukaryotic, the choice of host being dependent on yield, growth characteristics, availability of suitable vector systems, and the like. The same can be said of the choice of expression vector and the type of regulatory system used. For example, if desired, expression can be controlled in an inducible manner, to control the timing of expression during the cell culture process. Further variation available to the skilled artisan is the choice of accumulating the expressed protein within the cell or of causing its export into the cell culture medium. The purification method described herein is applicable to all such variants of host cell, regulation system and locus of expressed protein. The purification is exemplified with *E. coli* as host cells, transformed with a T7 polymerase driven expression vector in which expression of the inserted gene is inducible. The eIF-4E protein expressed in these conditions was located primarily within the host cells, rather than in the medium. A cell lysis step is therefore necessary. At least a portion of the eIF-4E protein can be obtained in soluble form from a host cell lysate without resorting to denaturing conditions. Subsequent purification of soluble eIF-4E can be obtained by chromatography, using affinity separation and chromatofocussing ion exchange chromatography. In the exemplified purification, affinity separation was carried out using m$^7$GTP Sepharose. Chromatofocussing ion exchange employed the FPLC system (fast protein liquid chromatography) with Mono Q (Pharmacia AB, Uppsala, Sweden) ion exchange resin. The purification yielded a single detectable band on SDS-PAGE, and a single component by isoelectric focussing.

Purified human eIF-4E binds to m$^7$GTP with an equilibrium binding constant of $10.1\pm0.3\times10^5 M^{-1}$ at pH 7.6 (20 mM HEPES buffer+1 mM DTT), 25° C. The result is similar (1.5–2 times higher) to results obtained using native human eIF-4E [Carberry, S. E. (1989) *Biochemistry* 28:8078–8083]. Therefore purified recombinant human eIF-4E readily and spontaneously binds m$^7$G-RNA under physiological conditions, in vitro. Single or multiple amino acid substitutions as taught herein can result in variants of eIF-4E having higher binding affinities of at least 4 times greater than naturally-occurring eIF-4E. Other single or multiple amino acid substitutions can result in decreased binding affinities for m$^7$G-RNA, without loss of other functions essential for initiating protein synthesis. Other sequence modifications, such as insertion or deletion of one or more amino acids can be employed, alone or in combination with amino acid substitution, to modify eIF-4E binding affinity for m$^7$G-RNA. The availability of milligram quantities of human eIF-4E or modified eIF-4E makes it possible to make enough eIF-4E-m$^7$G-RNA to render RNA transformation a practical reality. In principle, capped RNA (m$^7$G-RNA) encoding the desired amino acid sequence can be prepared from host cells expressing the desired amino acid sequence, or by a combination of in vitro transcription and capping reactions. In vitro transcription and capping reaction kits are commercially available, for example from Ambion, Austin, Tex. Binding eIF-4E to m$^7$G-RNA stabilizes the RNA, and increases the intracellular efficiency of translation, thereby enhancing the overall efficiency of RNA transfection. Various transfection methods are available to those skilled in the art and are applicable to transfection by eIF-4E-m$^7$G-RNA, of both cells in culture and cells in organized tissues and whole organisms.

Affinity chromatography provides a means for isolating proteins that bind eIF-4E. Purified eIF-4E can be cross-linked to a chromatographic matrix, for example agarose beads, and used as an affinity reagent. The technique has yielded several proteins from cell lysates that have characteristics of subunits of the eIF-4F complex. In particular, the isolation of p220 protein by eIF-4E affinity chromatography appears preferable to use of m$^7$GTP sepharose or the use of anti eIF-4E antibodies. Other proteins of interest that can also be isolated are eIF-4A, which is a subunit of eIF-4F, the 4E-BPs and other as yet uncharacterized regulatory proteins that are recruited to the 5' cap of translationally active mRNAs.

Having pure recombinant human or modified eIF-4E at hand makes it possible to generate polyclonal or monoclonal antibodies to eIF-4E. The antibodies are of value for detecting and measuring eIF-4E, for example on gels, in solution or in vivo. Assay methods can be employed wherein the analyte, eIF-4E, is labeled, for example with a radioactive precursor, or where the antibody itself is labeled, all according to methodology known in the art. Polyclonal antibodies to purified recombinant human or modified eIF-4E can immunoprecipitate both phosphorylated and non-phosphorylated forms of eIF-4E. Anti-eIF-4E can be used as an affinity reagent to provide an alternative affinity reagent for eIF-4E purification.

Studies on the binding site of eIF-4E have defined a sequence of amino acids, involved in binding m$^7$G-RNA extending approximately from positions 112–123, numbering from the translation start site. The region of amino acids involved in the binding of eIF-4E to m$^7$G-RNA was identified using photoaffinity labeling with a labeled analog, [$\gamma$-$^{32}$P] 8-N$_3$GTP. [Jayaram, B. et al. (1994) *J. Biol. Chem.* 269:3233–3242; Shoemaker, M. T. et al. (1993) *J. Biol. Chem.* 32:1883–1890; Salvucci, M. E. et al. (1992) *Biochemistry* 31:4479–4487]. The analog was found to bind to eIF-4E in competition with m$^7$GTP and with capped RNA. Furthermore, the binding site was saturated by the analog, indicating close approximation of the analog to the normal binding site. The analog binding to eIF-4E was rendered irreversible by a photo-chemical reaction and a tryptic peptide bearing the analog label was isolated by aluminum-III chelate chromatography and reverse phase HPLC. Once the binding region peptide was identified, it was then possible to employ alanine-scanning mutations to determine the contribution of specific amino acid residues to the binding, and to generate modified eIF-4E proteins with altered binding affinities. Modified eIF-4E analog proteins having either increased or decreased binding affinities have been made. For example, substitution of alanine for the naturally occurring tryptophan at position 113 (W 113 A) reduces affinity, while substitution of alanine or a polar but uncharged amino acid for a positively charged amino acid enhances binding affinity. Enhanced binding affinity can lead to increased capped RNA stability and increased duration of expression. Decreased binding affinity can be of value where sensitivity to regulatory influences is desired. Once the binding site has been identified it is straightforward to generate amino acid substitutions that have the desired binding characteristics with respect to m$^7$G-RNA. Accordingly, variant recombinant human eIF-4E is a part of the present invention.

Despite substantial progress in modeling the eIF-4E molecule in its native confirmation, the location of specific amino acid residues whose alteration affects binding affinity has remained unpredictable. Amino acid loci identified herein as significantly affecting m$^7$G-RNA binding differs from those previously identified on the basis of the cocrystal structure [Marcotrigiano, J. et al. (1997) *Cell* 89:951–961]. Further elucidation of critical loci can be obtained by site directed mutagenesis or by random mutagenesis, given the herein-enabled methods for expression, synthesis and purification of eIF-4E. eIF-4E/m$^7$GDP cocrystal structure suggested that a conserved hydrophobic surface feature on the concave dorsal face of eIF-4E is a potential site for interaction with eIF-4G and PHAS-I. Residues of eIF-4E that are proposed to participate in this binding include Val-69, Glu-70, Trp-73, Leu-131, Gly-139, Glu-140 and Asp-143 (Marcotrigiano et al., 1997, supra). The finding that substitution with alanine of the amino acid between residues 112 to 121 did not disrupt PHAS-I binding is consistent with the proposed binding site of PHAS-I. In addition, the observation that mutations in eIF-4E that altered binding to the m$^7$G cap structure did not impair the ability of eIF-4E to bind PHAS-I argues that the overall structure of the eIF-4E variants was maintained. The m$^7$GDP binding site of eIF-4E is located on the opposite side of the beta sheet from the PHAS-I binding site (Marcotrigiano et al. 1997 supra). Thus any changes in structure due to mutagenesis are probably localized to the side of the beta sheet that has the m$^7$G binding site.

The invention is set forth in further detail by description of specific embodiments as set forth in the following examples.

EXAMPLES

Materials—T7 polymerase driven prokaryotic expression vectors and BL21(DE3) strain of *E. coli* were obtained from Novagen (Madison, Wis.) and are described in detail elsewhere (Studier, F. W., et al. (1990) *Meth. Enzymol.* 185:60–89). IPTG was from Fisher Biotech. Hep G2 and 184A mammary carcinoma cells were from the American Type Culture Collection (Bethesda, Md.). Fetal bovine serum was from HyClone (Logan, Utah). m$^7$GTP and Protein A Sepharose were purchased from Pharmacia LKB Biotechnology Inc. (Piscataway, N.J.). m$^7$GDP was from Sigma Chemical Co. (St. Louis, Mo.). [$^{32}$P]Nucleotide triphosphates were from Dupont-NEN and [$^{35}$S]methionine was from ICN Biomedicals Inc. (Costa Mesa, Calif.). DNA sequencing reagents (Sequenase version 2.0) were from United States Biochemical (Cleveland, Ohio). A Coy Model 50 Tempocycler was used for the PCR studies.

Example 1: Construction of the eIF-4E$_{human}$ expression vector

Standard PCR methods were used to isolate an eIF-4E$_{human}$ cDNA with engineered 5' Nco I and 3' Bgl II restriction sites [Sambrook, J. et al. (1989) "Molecular Cloning—A Laboratory Manual" Cold Spring Harbor Press, Cold Spring Harbor, N.Y.; Faloona, F. et al. (1987) *Meth. Enzymol.* 155:335–350]. This permitted subcloning of the eIF-4E cDNA into an expression vector to produce wild-type eIF-4E. Template cDNAs of eIF-4E$_{human}$ were derived from both pTCEEC kindly provided by Robert Rhoads [Rychlik, W. et al. (1987) *Proc. Natl. Acad. Sci. USA* 84:945–949] and pCMV-SPORT provided by Deborah Polayes and Joel Jesse (Life Technologies, Gaithersburg, Md.). The PCR product was digested with Nco I and Bgl II, isolated using agarose gel electrophoresis and subcloned into the Nco I and Bam HI sites of pET-3d [Studier, F. W., et al. (1990) *Meth. Enzymol.* 185:60–89; Sambrook, J. et al. (1989) supra]. For expression, the BL21(DE3) strain of *E. coli* was transformed with this plasmid. DNA sequence analysis confirmed that the plasmid encodes the original sequence reported for human eIF-4E [Rychlik, W. et al. (1987) supra].

Example 2: Expression and purification of functional recombinant eIF-4E$_{human}$ Purification was carried out essentially as described by Hagedorn, et al. (1997) *Protein Expression and Purif.* 9:53–60, which is incorporated herein by reference. BL21 (DE3) cells expressing human eIF-4E were grown in M9ZB media with ampicillin to an OD$_{600}$ of 0.6–0.7 at which time cultures were induced with 0.4 mM IPTG [Studier, F. W. et al. (1990) supra]. FIG. 1 shows polyacrylamide gel separation of whole cell lysates at 0, 2 and 3 hours after induction. Culture media was centrifuged at 500×g for 15 min, and *E. coli* pellets were suspended in 3 ml of 50 mM Tris-HCl pH 8.0, 100 mM KCl, 1 mM EDTA, 1 mM DTT, 1 mM PMSF, and 0.1 mg/ml lysozyme per gram wet weight. Samples were stirred intermittently on ice for 15 min and sonicated. Triton X-100 was added to a final concentration of 0.1%. The samples were mixed for 15 min at 4° C. and centrifuged at 15,000 rpm in a Sorvall SS-34 rotor for 20 min. Supernatants were used as starting material for subsequent chromatography purification steps.

Figure 2:
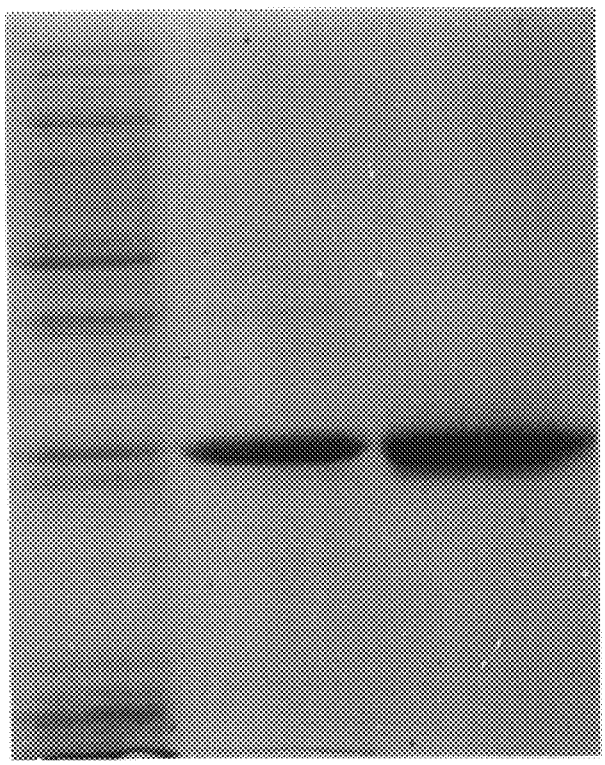
FIG. 2 shows purification of functional recombinant eIF-4E. A photograph is shown of a Coomassie blue stained 12% polyacrylamide gel of proteins present in starting material (*E. coli* lysate) (lane 1, 20 μg), $m^7$GTP Sepharose affinity purified eIF-4E (lane 2, 20 μg) and mono Q FPLC purified (lane 3, 25 μg).
Figure 3:
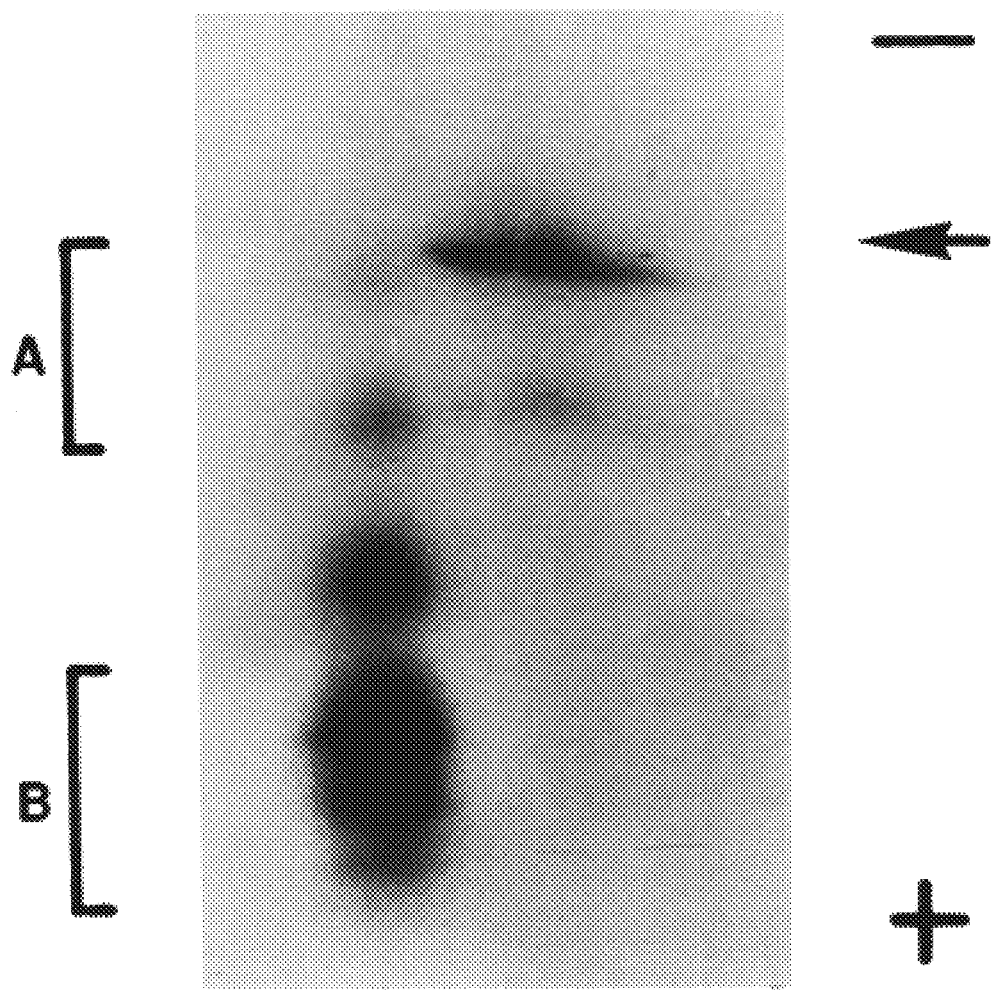
FIG. 3 shows isoelectric focusing analysis of recombinant eIF-4E. A representative analysis of recombinant eIF-4E (lane 2) and eIF-4E isolated from rabbit reticulocyte lysate (lane 1) is shown. An arrow indicates the location of recombinant eIF-4E. (A) designates the region where unphosphorylated and (B) the region where phosphorylated eIF-4E concentrate (Bu et al. (1992) *FEBS Lett.* 301:15–18; Mick et al. (1998) *FEBS Lett* 236:484–488)).

In the first chromatography step we used m⁷GTP Sepharose as described in detail previously [Haas, D. W. et al. (1991) *Arch. Biochem. Biophys.* 284:84–89]. eIF-4E was eluted during m⁷GTP Sepharose chromatography with m⁷GDP. Fractions were analyzed by SDS-PAGE and Coomassie Blue staining and those containing eIF-4E were concentrated using a Centriprep-10 concentrator. The concentrated protein was applied to a Mono Q HR5/5 FPLC column in 50 mM HEPES-pH 8.0, 1 mM $MgCl_2$, and 1 mM DTT at a flow rate of 0.3 ml/min. Following a wash step with the same buffer, proteins were eluted with a 34 ml linear gradient of 0–500 mM NaCl at 0.3 ml/min in the same buffer. Fractions containing eIF-4E were identified by SDS-PAGE analysis. Results of the purification process are shown in Table 1. FIG. 2 shows polyacrylamide gel analysis of *E. coli* lysate, affinity-purified eIF-4E. FIG. 3 shows results of an isoelectric focussing analysis of eIF-4E purified on FPLC.

TABLE I

Purification table for recombinant eIF-4E expressed in *E. coli*.

|  | Volume (ml) | Total protein Concentration (mg/ml)* | Quantity of eIF-4E (mg)* | Recovery of soluble eIF-4E (%) |
|---|---|---|---|---|
| *E. coli* culture | 1000 | — | — | — |
| Soluble lysate | 50 | 10 | 4 | 100 |
| m⁷GTP Affinity column | 3 | 0.9 | 2.5 | 63 |
| Mono Q FPLC | 1 | 2.1 | 2.0 | 50 |

*Protein concentrations were estimated using the Bradford method and the values given are from a representative experiment (Haas, D. W. et al. (1991) Arch. Biochem. Biophys. 284: 84–89).
Note: Approximately 1–5% of the eIF-4E expressed in *E. coli* was soluble as estimated by Coomassie blue staining of SDS-PAGE analyzed samples.

Example 3: Fluorescence measurements

Figure 4A:
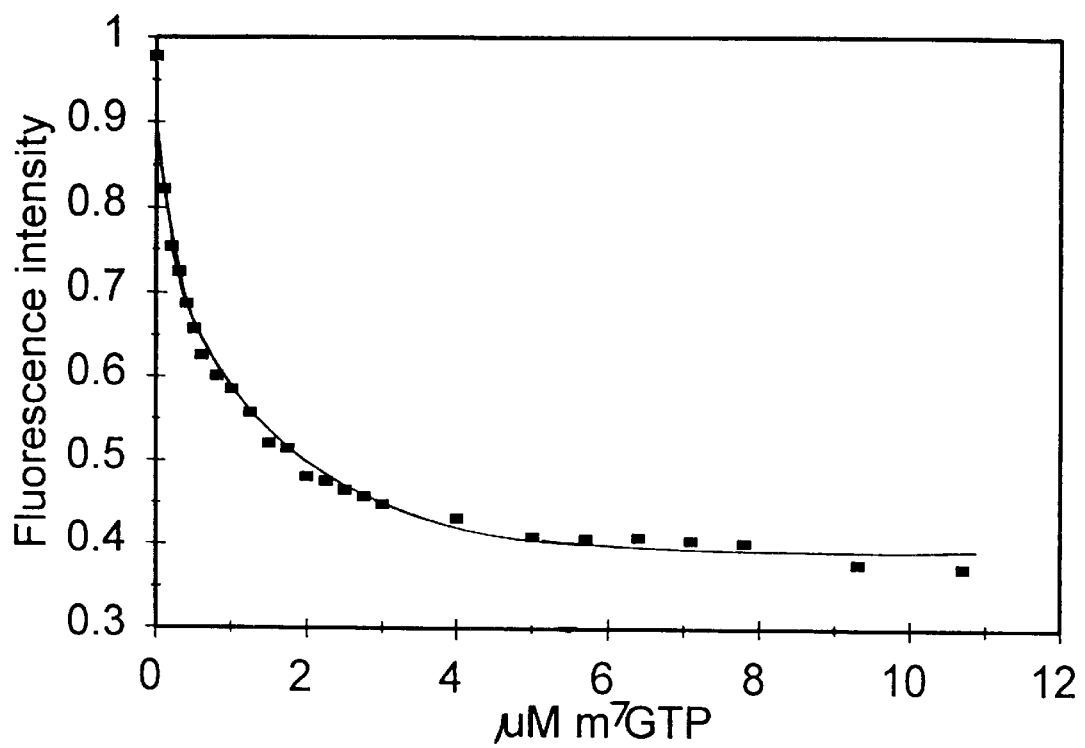
FIGS. 4A and 4B.
Figure 4B:
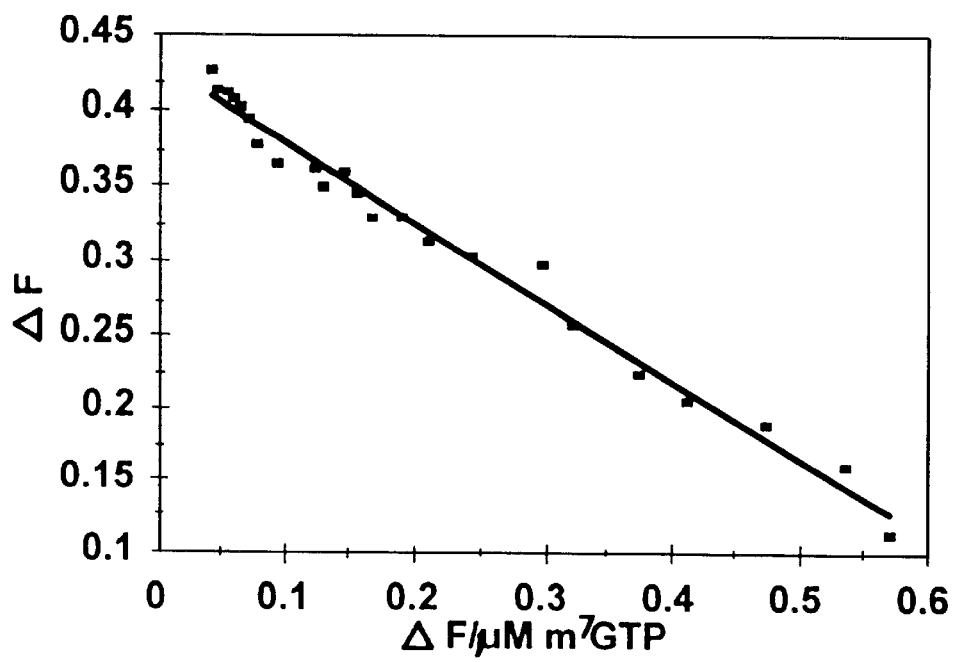

Fluorescence measurements were made at 25° C. on a SPEX Fluorolog-T2 spectrofluorometer equipped with a high intensity (450 w) xenon arc lamp. An excitation wave length of 280 nm was used to monitor the tryptophan fluorescence emission of recombinant eIF-4E at 330 nm. Excitation and emission slit widths of 1.4 and 2.0 mm respectively were used and a 1.0 cm sample cell pathlength was employed. The buffer used for all fluorescence measurements was 20 mM HEPES at pH 7.6 and 1 mM DTT (designated Buffer A in FIG. 4). The steady state data were collected and analyzed as described previously [Carberry, S. E. et al. (1989) Biochemistry 28:8078–8083; Carberry, S. E. et al. (1990) *Biochemistry* 29:3337–3341. An excitation wavelength of 289 nm was used to monitor the tryptophan fluorescence emission of the proteins. Excitation and emission slit widths of 1.5 mm and 2.0 mm respectively were used and cell path length was 1.0 cm. The results are shown in FIG. 4.

Figure 5:
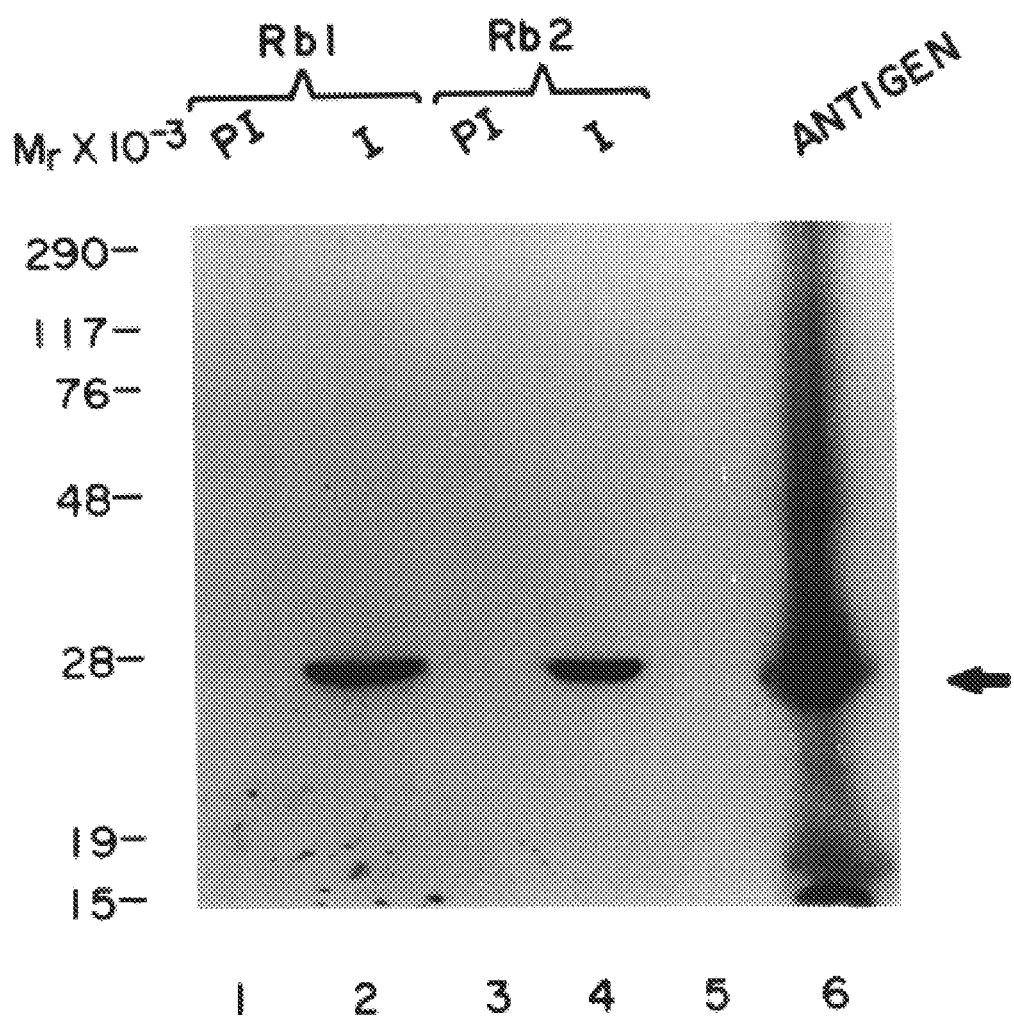
FIG. 5 shows production of immunoprecipitating anti-eIF-4E rabbit serum using recombinant eIF-4E. $^{35}$S-labeled eIF-4E (arrow) prepared in reticulocyte lysates was used in immunoprecipitation assays with preimmune (PI) or immune (I) rabbit serum from two rabbits (Rb 1 & 2) (lanes 1–4). An autoradiogram of the samples analyzed by SDS-PAGE is shown. Lane 6 represents the quantity of [$^{35}$S]eIF-4E present in each incubation and lane 5 is a blank lane.

Example 4: Immunizations and purification of monospecific rabbit anti-eIF-4E antibodies Two female New Zealand white rabbits were immunized by s.c. injections as described in detail elsewhere [Hagedorn, C. H. et al. (1990) *FEBS Lett.* 264:59–62]. FPLC or SDS-PAGE purified recombinant eIF-4E$_{human}$ was suspended in a 50% emulsion of adjuvant in phosphate buffered saline and used for immunizations. Between 100 and 400 μg of protein were used per animal for each immunization. Booster immunizations were given at 4–6 week intervals. FIG. 5 shows results of immunoprecipitation of labeled recombinant human eIF-4E using immune serum of two different rabbits.

Preparation of recombinant eIF-4E and antibody affinity beads

Recombinant eIF-4E that was purified by FPLC was covalently crosslinked to agarose beads (AminoLink, Pierce Chemical Co.) following the instructions provided by the manufacturer. Protein A Sepharose (Pharmacia Biotech) was pre-incubated with rabbit pre-immune or anti-eIF-4E serum in lysis buffer (described below) and then washed three times prior to use in these studies.

Example 5: Metabolic labeling of mammalian cells

Hep G2 and 184A mammary carcinoma cells were cultured as described elsewhere [Bu. X. et al. (1993) *J. Biol. Chem.* 268:4975–4978]. Cells (75 mm² flasks) were incubated overnight in 3 ml of minimal essential medium without methionine, containing 5% complete medium and 0.3 mCi/ml of [³⁵S]methionine/cysteine. Media was removed, cell monolayers rinsed twice with phosphate buffered saline and then lysed as described in the next section.

Figures 6A, 6B:
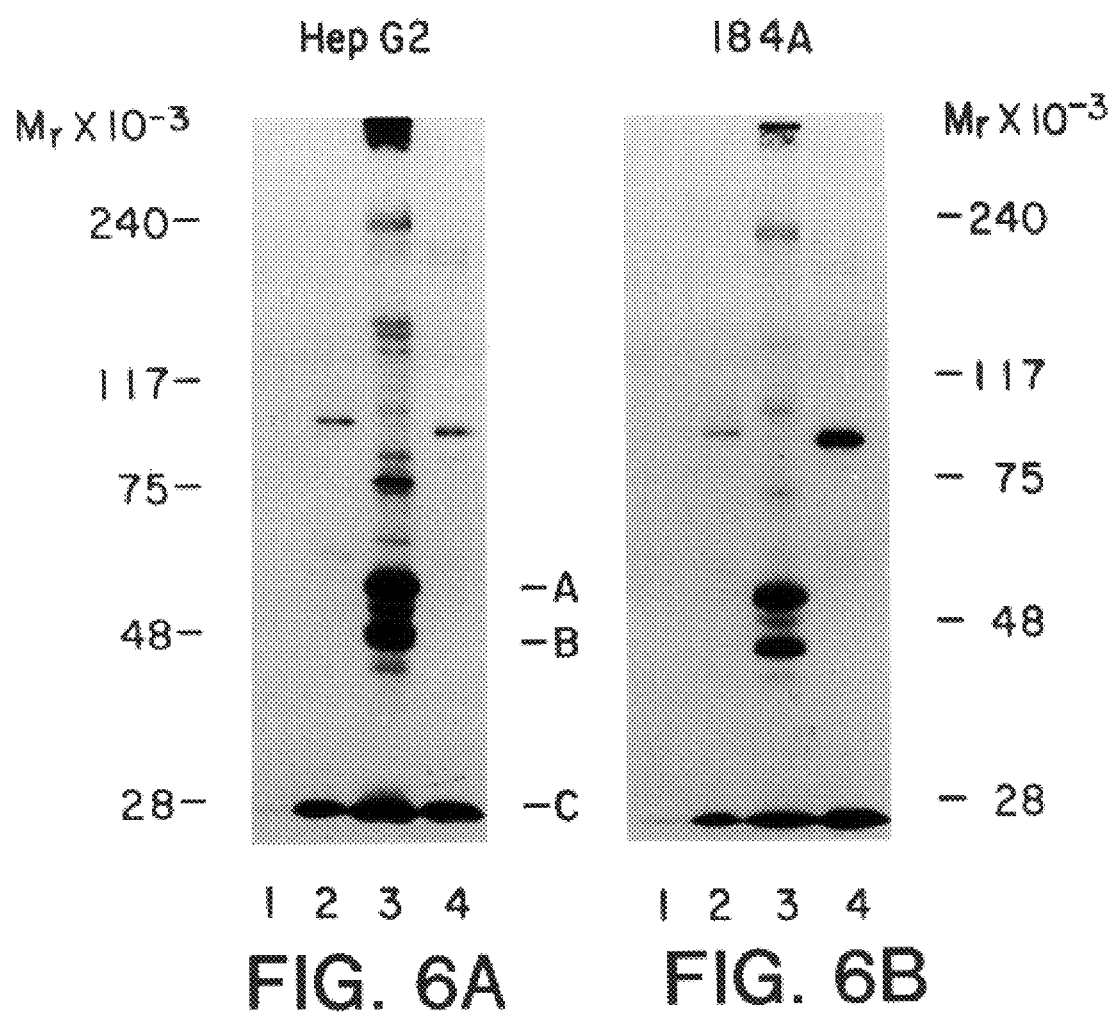
FIGS. 6A and 6B show isolation of eIF-4E binding proteins. Mammary carcinoma (184A, FIG. 6A) and Hep G2 (FIG. 6B) cells were labeled with [$^{35}$S]methionine/cysteine. Equal aliquots of cell lysates were mixed at 4° C. with Protein A Sepharose prebound with rabbit preimmune (lane 1) or anti-eIF-4E serum (lane 2), recombinant eIF-4E agarose beads (lane 3), and $m^7$GTP Sepharose (lane 4). After washing, proteins bound to beads were analyzed by SDS-PAGE and autoradiography.

Isolation of proteins that bind recombinant eIF-4E, anti-eIF-4E antibody and m⁷GTP affinity beads Media was removed from labeled cell, rinsed twice with phosphate buffered saline and then lysed on ice (20 min) using 4 ml of lysis buffer (20 mM HEPES at pH 7.4, 0.5% Triton X-100, 100 mM KCl, 2 mM $MgCl_2$, 50 mM β-glycerolphosphate, 0.5 mM DTT, 1 mM PMSF, 10 μg/ml leupeptin and 10 μg/ml aprotinin). Lysates were centrifuged for 15 min at 10,000×g (4° C.) and the supernatants removed and divided into four equal aliquots in microfuge tubes. Protein A Sepharose antibody beads, recombinant eIF-4E beads, or m⁷GTP Sepharose beads were mixed with lysates at 4° C. for 45 min. Affinity beads were pelleted by centrifugation for 15 sec in a microfuge and washed three times with lysis buffer. Proteins bound to beads were then analyzed by SDS-PAGE and autoradiography [Haas. D. W. et al. (1991) supra]. The results are shown in FIG. 6. FIG. 7 shows identification of p220 based on proteolysis of p220 in poliovirus-infected cells.

Example 6: Modification of eIF-4E Binding Affinity

A number of individual amino acids in the region 112–123 were substituted by alanine, using the technique of alanine-scanning mutagenesis. Binding constants of the various mutants (variants) were measured. Results are shown in Table 2. We expressed and purified milligram quantities of most eIF-4E$_{human}$ variants for detailed analysis using *E. coli* BL21(DE3)cells transformed with pET-3d vectors. Cells were cultured, induced with IPTG and lysed in SDS-PAGE sample buffer as described in Example 2. Samples of cells were analyzed by SDS-PAGE and Coomassie blue staining. W113A, L117A, Q120A and Q121A were consistently expressed at levels 3–4 times more than wild-type eIF-4E, while L114A expression was lower. The level of expression of the other variants was similar to that of wild-type eIF-4E.

In order to assess the solubility of each variant, cells were lysed and centrifuged as described supra. Supernatants prepared from equivalent wet weights of cells were analyzed by SDS-PAGE and Western blotting with anti-eIF-4E antibodies. Supernatants from all variants contained soluble eIF-4E. The lower amount of soluble L114A and the greater amounts of Q120A and Q121A detected are consistent with their respective lower and higher levels of expression. W113A and L117A variants, on the other hand, had high expression levels, but the amount of soluble protein in the lysate was similar to that of wild-type eIF-4E. Except for the W113A and L117A variants, no major differences in solubility were observed among the other alanine variants studied.

Milligram quantities of eIF-4E variants were purified by $m^7$GTP-Sepharose affinity chromatography and Resource Q FPLC as described for the recombinant wild-type protein [Hagedorn, C. H. et al. (1997) *Protein Expression and Purif.* 9:53–60]. Analysis of the variants by SDS-PAGE demonstrated a high degree purity except for W113A and L117A. This property of W 113A made it impractical to obtain sufficient quantities of the variant for further purification. The yield of W113A from a one liter culture of *E. coli* was approximately 10 μg, while the yield for wild-type eIF-4E was 102 mg. The yields of purification (mg protein/liter culture) using $m^7$GTP affinity chromatography were also low for I115A and L117A. These initial results suggested that the W113A, 115A and L117A variants had an impaired ability to bind mRNA caps as compared to wild-type eIF-4E. The lower solubility of W113A and L117A suggest that these variations disrupted the folding of the protein rather than having a direct effect on cap binding. It is noteworthy that even though L117A was processed using the same purification steps as the other variants, it was considerably less pure after the final step. This was largely due to poor binding in the first affinity step.

Circular dichroism analysis: The structural integrity of the variant proteins was assessed by a spectral method, circular dichroism (CD). Structural comparisons of I115A, T116A, N118A and K119A revealed that they are all very similar to the wild-type of eIF-4E in both free and $m^7$GTP-bound forms. W113A and L117A were not analyzed because of difficulties in purifying these variant proteins.

Affinity of eIF-4E variants for the mRNA cap: The binding of each variant to the mRNA cap structure was first examined by a $m^7$GTP-Sepharose binding assay at 4° C. *E. coli* lysates containing equivalent quantities of eIF-4E protein were incubated with an excess of $m^7$GTP-Sepharose. Proteins that bound to $m^7$GTP-Sepharose were analyzed by SDS-PAGE and Coomassie Blue staining. The results demonstrated that the W113A variant barely bound to $m^7$GTP-Sepharose, and that I115A and L117A variants exhibited reduced binding as compared to wild-type eIF-4E. This is consistent with the low yields of W113A, I115A and L117A obtained during purification of these variants. The binding of all other variants to $m^7$GTP-Sepharose was comparable to that of wild-type eIF-4E.

The preparation of large quantities of recombinant eIF-4E variants allowed us to directly determine the Kd of binding to the mRNA cap structure. Quantitation was performed by measuring the fluorescence quenching of intrinsic tryptophan residues in eIF-4E upon $m^7$GTP binding at 25≈ C. (Example 3). The $K_d$ values of wild-type and variant eIF-4E for $m^7$GTP are shown in Table 1. Except for two variants, these results were consistent with those obtained by $m^7$GTP-Sepharose binding assays. The exceptions were Q120A and Q121A which had lower affinities for $m^7$GTP than suggested by the $m^7$GTP-Sepharose binding assays. This is possibly a consequence of a lower stability of these variants at the higher temperature in the fluorescence quenching assay.

Ability of eIF-4E variants to bind PHAS-I: The binding of PHAS-I, a translational repressor protein, to eIF-4E regulates translation and gene expression. To determine if mutagenesis of amino acids in the 112–121 region of eIF-4E affected the PHAS-I binding region we examined the ability of each variant to bind PHAS-I. Lysates of *E. coli* expressing wild-type or eIF-4E variants were mixed with *E. coli* lysate containing recombinant PHAS-I and immunoprecipitated with anti-PHAS-I antibodies. Samples were analyzed by SDS-PAGE followed by immunoblotting with anti-eIF-4E antibodies. All eIF-4E variants were able to bind PHAS-I at a level similar to that of wild-type. The amount of PHAS-I immunoprecipitated in these samples was shown to be very similar by stripping and reprobing the nitrocellulose membranes with anti-PHAS-I antibodies. These results indicate that mutagenesis of the Arg-112 to Gln-121 region of eIF-4E did not disrupt its interaction with PHAS-I.

Translational activity of eIF-4E variants: The ability of eIF-4E variants to initiate translation was examined in rabbit reticulocyte lysates which were depleted of endogenous eIF-4E by $m^7$GTP-Sepharose chromatography [Svitkin Y. V. et al. (1996) *EMBO J.* 15:7147–7155]. Western blotting analysis using anti-eIF-4E antibodies detected no eIF-4E in lysates after chromatography. The addition of wild-type eIF-4E to the translation mixture resulted in 2–4 fold increase in the translation of globin mRNA. This increase in translation was cap-dependent since addition of $m^7$GDP inhibited the eIF-4E-dependent translation. The relative abilities of eIF-4E variants to restore globin mRNA translation were tested for all variants except W113A. Except for L117A, all variants were able to initiate translation to a level similar to that of wild-type eIF-4E.

Cell-free translations: Nuclease-treated rabbit reticulocyte lysates (Promega) were depleted of endogenous eIF-4E by chromatography on $m^7$GTP-Sepharose according to the previously described protocol (Svitkin et al. 1996, supra). Aliquots of eIF-4E-depleted lysates were stored in liquid nitrogen vapor. eIF-4E depletion was verified by Western blotting analysis (data not shown). Cell-free translations were performed at 30° C. as described in detail in the Promega technical manual. Reaction mixtures contained 75 ng wild-type or variant eIF-4E (FPLC purified), 80 ng/ml globin mRNA, 10 μCi [$^{35}$S]methionine (>1000 Ci/mmol, ICN) and 10 μl reticulocyte lysate in a final volume of 16 μl. In the case of L117A, which was not highly purified, a sufficient quantity of the preparation was added to approximate 75 ng of L117A. As a control for cap-dependent translation, 1 mM $m^7$GTP was added to a complete incubation containing wild-type eIF-4E. Following 60 min of incubation at 30° C., 7 μl of the reaction mixture were spotted on a 1 cm² Whatman 3 MM filter paper and air dried for 10 min. Filters were soaked in 5% trichloroacetic acid (TCA) with 1 mM methionine for 10 min on ice, rinsed with fresh 5% TCA and then boiled for 10 min in 5% TCA. Following another wash with 5% TCA, filters were rinsed with 95% ethanol and then with acetone. Dried filter papers were placed in vials with scintillation liquid and [$^{35}$S] methionine incorporated into protein was quantitated by liquid scintillation spectrometry.

TABLE 2

| Amino acid replacement | Binding constant $K_d$ (μM) | Wild type amino acid |
| --- | --- | --- |
| Wild type | 0.14 | |
| R112 → A | 0.11 | Positively charged |
| W113 → A | Very low binding | Hydrophobic |
| L114 → A | 0.11 | Hydrophobic |
| I115 → A | 0.31 | Hydrophobic |

TABLE 2-continued

| Amino acid replacement | Binding constant $K_d$ ($\mu$M) | Wild type amino acid |
|---|---|---|
| T116 → A | 0.14 | Polar, uncharged |
| L117 → A | 0.20 | Hydrophobic |
| N118 → A | 0.07 | Polar, uncharged |
| K119 → A | 0.04 | Positively charged |
| Q120 → A | 0.22 | Polar, uncharged |
| Q121 → A | 0.37 | Polar, uncharged |

Further modifications and variations can be made according to the principles and teachings disclosed herein, including, but not limited to, improvements in yield of soluble eIF-4E from lysate, other kinds of amino acid substitution, both as to locus and identify of substituent amino acid, and improvements and optimization of RNA transfection using eIF-4E-m$^7$G-RNA or variant eIF-4E-m$^7$G-RNA.

We claim:

1. An isolated nucleic acid molecule encoding a variant human eIF-4E protein having altered binding affinity for m$^7$G-RNA compared to natural human eIF-4E protein, wherein said variant protein has an amino acid substitution in the region of amino acids 112 and 114–121.

2. The isolated nucleic acid molecule of claim 1 encoding a variant human eIF-4E having an amino acid substitution of alanine for asparagine at amino acid position number 118.

3. The isolated nucleic acid molecule of claim 1 encoding a variant human eIF-4E having an amino acid substitution of alanine for lysine at amino acid position number 119.

4. The isolated nucleic acid molecule of claim 1 encoding a variant human eIF-4E having an amino acid substitution of alanine for isoleucine at amino acid position number 115.

5. The isolated nucleic acid molecule of claim 1 encoding a variant human eIF-4E having an amino acid substitution of alanine for glutamine at amino acid position number 121.

* * * * *

UNITED STATES PATENT AND TRADEMARK OFFICE
CERTIFICATE OF CORRECTION

PATENT NO. : 6,596,854 B2
DATED : July 22, 2003
INVENTOR(S) : Hagedorn et al.

It is certified that error appears in the above-identified patent and that said Letters Patent is hereby corrected as shown below:

Title page, Item [54] and Column 1, lines 1-4,
Please replace the title "ISOLATED NUCLEIC ACID MOLECULE ENCODING A VARIANT HUMAN EUKARYOTIC INTIATION FACTOR 4E PROTEIN" with -- ISOLATED NUCLEIC ACID MOLECULE ENCODING A VARIANT HUMAN EUKARYOTIC INITIATION FACTOR 4E PROTEIN --.

Title page,
Item [22], replace the Filing Date of "Apr. 14, 2001" with -- May 14, 2001. --

Column 11,
Line 54, replace "25≅C" with -- 25ºC --.

Signed and Sealed this

Twenty-eighth Day of October, 2003

JAMES E. ROGAN
*Director of the United States Patent and Trademark Office*